(12) United States Patent
Meyer (10) Patent No.: US 8,539,954 B2
(45) Date of Patent: Sep. 24, 2013

(54) BREATHING ASSISTANCE APPARATUS

(76) Inventor: Vincent Meyer, Murdock, NE (US)

(*) Notice: Subject to any disclaimer, the term of this patent is extended or adjusted under 35 U.S.C. 154(b) by 532 days.

(21) Appl. No.: 12/795,084

(22) Filed: Jun. 7, 2010

(65) Prior Publication Data

US 2011/0297159 A1 Dec. 8, 2011

(51) Int. Cl.
*A62B 25/00* (2006.01)

(52) U.S. Cl.
USPC .................................................... 128/207.14

(58) Field of Classification Search
USPC ............ 128/200.24, 200.26, 206.29, 207.14, 128/207.15, 848, 859, 861, 862; 600/560
See application file for complete search history.

(56) References Cited

U.S. PATENT DOCUMENTS

| | | | | |
|---|---|---|---|---|
| 3,106,916 A | * | 10/1963 | Matthes | 128/202.28 |
| 4,071,026 A | | 1/1978 | Bevins | |
| 4,170,230 A | * | 10/1979 | Nelson | 128/859 |
| 4,261,354 A | * | 4/1981 | Nelson | 128/203.23 |
| 4,275,725 A | * | 6/1981 | Nelson | 128/207.14 |
| 4,289,127 A | * | 9/1981 | Nelson | 128/207.14 |
| 5,309,906 A | * | 5/1994 | LaBombard | 128/207.14 |
| 5,743,258 A | | 4/1998 | Sato et al. | |
| 5,792,067 A | * | 8/1998 | Karell | 600/534 |
| 6,494,209 B2 | * | 12/2002 | Kulick | 128/848 |
| 6,536,424 B2 | | 3/2003 | Fitton | |
| 6,772,761 B1 | * | 8/2004 | Rucker, Jr. | 128/207.14 |
| 6,820,617 B2 | | 11/2004 | Robertson et al. | |
| D504,947 S | | 5/2005 | McAuley et al. | |
| 6,981,502 B2 | | 1/2006 | McCormick et al. | |
| 6,997,186 B2 | | 2/2006 | Robertson et al. | |
| 7,328,698 B2 | | 2/2008 | Scarberry et al. | |
| 7,451,766 B2 | | 11/2008 | Miller | |
| 2002/0139375 A1 | | 10/2002 | Kulick | |
| 2005/0150504 A1 | * | 7/2005 | Heeke et al. | 128/848 |
| 2006/0282010 A1 | * | 12/2006 | Martin et al. | 600/560 |
| 2009/0120446 A1 | * | 5/2009 | Vaska et al. | 128/848 |
| 2010/0043804 A1 | * | 2/2010 | Razmovski | 128/848 |
| 2010/0101567 A1 | * | 4/2010 | Hauge | 128/200.26 |
| 2011/0073113 A1 | * | 3/2011 | Pell | 128/207.14 |

FOREIGN PATENT DOCUMENTS

| | | |
|---|---|---|
| GB | 1248474 | 10/1971 |
| JP | 10167179 | 6/1998 |

OTHER PUBLICATIONS

Oropharyngeal Airway (OPA), School of Medicine University of Virginia, http://www.healthsystem.virginia.edu/internet/anestesiology-elective/airway/equipment.cfm, 4 pages printed from the internet on Jan. 31, 2010.

* cited by examiner

*Primary Examiner* — Justine Yu
*Assistant Examiner* — Christopher Miller (57) ABSTRACT

The disclosure describes a novel apparatus for providing an airway to a patient after having his or her jaw wired shut. The apparatus provides for an unobstructed airway that allows a patient with at least a partially blocked nasal passage to breathe effectively and easily during recovery.

16 Claims, 6 Drawing Sheets

BREATHING ASSISTANCE APPARATUS

INTRODUCTION

Several medical procedures, such as surgery, require the wiring of a patient's jaw shut. A patient with a wired jaw has limited means of accessing air for breathing. The patient may be able to access air through the patient's nasal cavity. However, if the nasal cavity becomes inflamed, swollen, and/or blocked, the air flow through the patient's nasal cavity may be blocked or limited.

If the nasal cavity becomes blocked or provides limited air passage, the patient must breathe through their mouth. Behind the teeth, a passageway exists between the molars and the back of mouth. This passageway remains open even when a jaw is wired shut. However, patients who require their mouths to be wired shut often experience swelling in their mouths limiting the patient's access to this air flow path.

If the patient cannot receive enough air from either of these two areas an additional procedure must be performed that cuts a direct air flow path through the skin of the patient to their trachea (i.e. commonly referred to as "being trached"). Medical care-givers prefer not to perform invasive procedures on otherwise healthy patients, unless absolutely necessary.

SUMMARY

The disclosure describes a novel apparatus for providing an airway to a patient after having his or her jaw wired shut. The apparatus provides for an unobstructed airway that allows a patient with at least a partially blocked nasal passage to breathe effectively and easily during recovery.

In part, this disclosure describes a breathing assistance apparatus, including:

a right airway tubing including a right interior airway opening, a right exterior airway opening, and a right passageway connecting the right interior airway opening and the right exterior airway opening, the right passageway including a right exit tube, a right inner flat passageway wall connected to the right exit tube, and a right outer curved passageway wall connected to the right flat passageway wall and the right exit tube;

a left airway tubing including a left interior airway opening, a left exterior airway opening, and a left passageway connecting the left interior airway opening and the left exterior airway opening, the left passageway including a left exit tube, a left flat passageway wall connected to the left exit tube, and a left curved passageway wall connected to the left flat passageway wall and the left exit tube; and a connector, the connector attaching the right airway tubing to the left airway tubing.

The right passageway provides a flow path for air to move to and from behind a right side of a patient's teeth via the right interior airway opening through the patient's mouth via the right exterior airway opening during use and the left passageway provides a flow path for air to move to and from behind a left side of a patient's teeth via the left interior airway opening through the patient's mouth via the left exterior airway opening during use Another aspect of this disclosure describes a breathing assistance apparatus, including:

a left airway tubing, the left airway tubing including a left interior airway opening, a left exterior airway opening, and a left passageway connecting the left interior airway opening and the left exterior airway opening, the left passageway including a left exit tube, a left outer passageway wall connected to the left exit tube, and a left inner passageway wall connected to the left outer passageway wall and the left exit tube;

a left airway tubing including a left interior airway opening, a left exterior airway opening, and a left passageway connecting the left interior airway opening and the left exterior airway opening, the left passageway including a left exit tube, a left inner passageway wall connected to the left exit tube, and a left outer passageway wall connected to the left inner passageway wall and the left exit tube; and a connector, the connector attaching the left airway tubing to the left airway tubing.

The left passageway provides a flow path for air to move to and from behind a left side of a patient's teeth via the left interior airway opening through the patient's mouth via the left exterior airway opening during use and The left passageway provides a flow path for air to move to and from behind a left side of a patient's teeth via the left interior airway opening through the patient's mouth via the left exterior airway opening during use In yet another aspect, the disclosure describes a breathing assistance apparatus including:

a left interior airway opening;
a right interior airway opening;
an exterior airway opening;
an exit tube wall, the exit tube wall forming the exterior airway opening;
an inner flat passageway wall connecting the left interior airway opening and the right interior airway opening;
a left curved passageway wall connecting the left interior airway opening to the exit tube wall and attached to the inner flat passageway wall;
a right curved passageway wall connecting the right interior airway opening to the exit tube wall and attached to the inner flat passageway wall; and
an air passageway formed by the inner flat passageway wall, the left curved passageway wall, the right curved passageway wall, and the exit tube and connecting the left interior airway opening, the right interior airway opening, and the exterior airway opening to each other.

The air passageway provides a flow path for air to move to and from behind a patient's teeth via the left and right interior airway openings and through the patient's mouth via the exterior airway opening during use.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

DETAILED DESCRIPTION

Although the device introduced and discussed in detail below may be implemented after a variety of surgeries or medical procedures, the present disclosure will discuss the implementation of this apparatus in the context of providing an airway to a human patient. The reader will understand that the technology described in this device for human patients could be adapted for use with other surgeries or procedures for non-human patients.

As discussed above, patients who have had their jaws wired shut may have difficulty breathing if their nasal cavity becomes blocked or partially blocked. When the jaw is wired shut, the patient has a space on each side of his or her mouth that could potentially act as an airway. This space is located between the back teeth and the back of the patient's mouth. This space, however, may also become blocked, hindered, and/or swollen due to swelling and or inflammation in the mouth caused by the medical procedure or illness. Accordingly, patients with a wired shut jaw may have difficulty breathing if their nose become blocked, clogged, and/or partially clogged. Physicians prefer not to perform any invasive surgeries if unnecessary. Accordingly, it is desirable to provide a breathing apparatus that can provide an airway through the mouth of a patient even during swelling and/or inflammation.

The breathing apparatus as described herein provides patients with an unobstructed airway. This allows patients to relax and breathe more effectively for better recovery. Further, the breathing apparatus described herein may prevent the need for an invasive surgery to provide an airway to patients and thereby decrease recovery time and medical costs.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples.

While various embodiments have been described for purposes of this disclosure, various changes and modifications may be made which are well within the scope of the present disclosure. Numerous other changes may be made which will readily suggest themselves to those skilled in the art and which are encompassed in the spirit of the disclosure.

Unless otherwise indicated, all numbers expressing quantities, properties, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure.

FIGS. 1-4 illustrate an embodiment of a breathing apparatus 100. Breathing apparatus 100 maybe inserted into a patient's mouth with a wired shut jaw to provide a breathing airway for the patient. Breathing apparatus 100 is inserted into the mouth and rests next to the outside of a patient's teeth 122. Further, breathing apparatus 100 is adaptable to provide for a breathing airway on one side or both sides of a patient's mouth.

Breathing apparatus 100 may be made of any suitable semi-rigid material for insertion in a patient's mouth. In one embodiment, the material is a semi-rigid plastic. Further, the breathing apparatus may be made in any suitable size to provide a breathing airway for the patient. Accordingly, the size may vary for use with children, infants, adults, men, or women.

Breathing apparatus 100 includes a right airway tube 101, a left airway tube 111, and a connector 110. The right airway tube 101 and the left airway tube 111 may be configured to provide for easy size adjustments based on patient mouth size. In one embodiment, airway tubes 101, 111 are made of a material that may be cut with scissors, a knife, and/or a razor. This embodiment, allows any end of the airway tubes 101, 111 to be cut and shortened as needed. Accordingly, this embodiment, allows the breathing apparatus 100 to be easily adjusted for different mouth sizes prior to use for a more effective airflow and a more comfortable mouth fit for the patient.

In another embodiment, the right airway tube 101 and the left airway tube 111 are substantially mirror images of each other. As utilizes herein, the term "substantially mirror images" refers to an airway tube that is mirrors enough of the opposite airway tube that it can be utilized on either side of a patient's mouth. In this embodiment, right airway tube 101 and left airway tube 111 may be utilized separately or in combination on either side of a patient's mouth.

The right airway tube 101 includes a right interior airway opening 102, a right exterior airway opening 105, and a right passageway 104. Right passageway 104 provides a flow path for air from the right interior airway opening 102 to the right exterior airway opening 105. This flow path allows air to travel to and from the inside of the patient's mouth to the exterior of the patient mouth during use.

The right exterior airway opening 105 is positioned so that during use it is located outside of a patient's mouth. The right interior airway opening 102 is positioned so that during use the right interior airway opening 102 is located adjacent to, extends into, or extends through the space behind one-side of teeth 124 and the back of the patient's mouth on that side before becoming the throat. Behind the teeth 124, is a position located behind the last upper and lower tooth on one side of the patient's mouth that is closest to a patient's throat.

Figure 1:
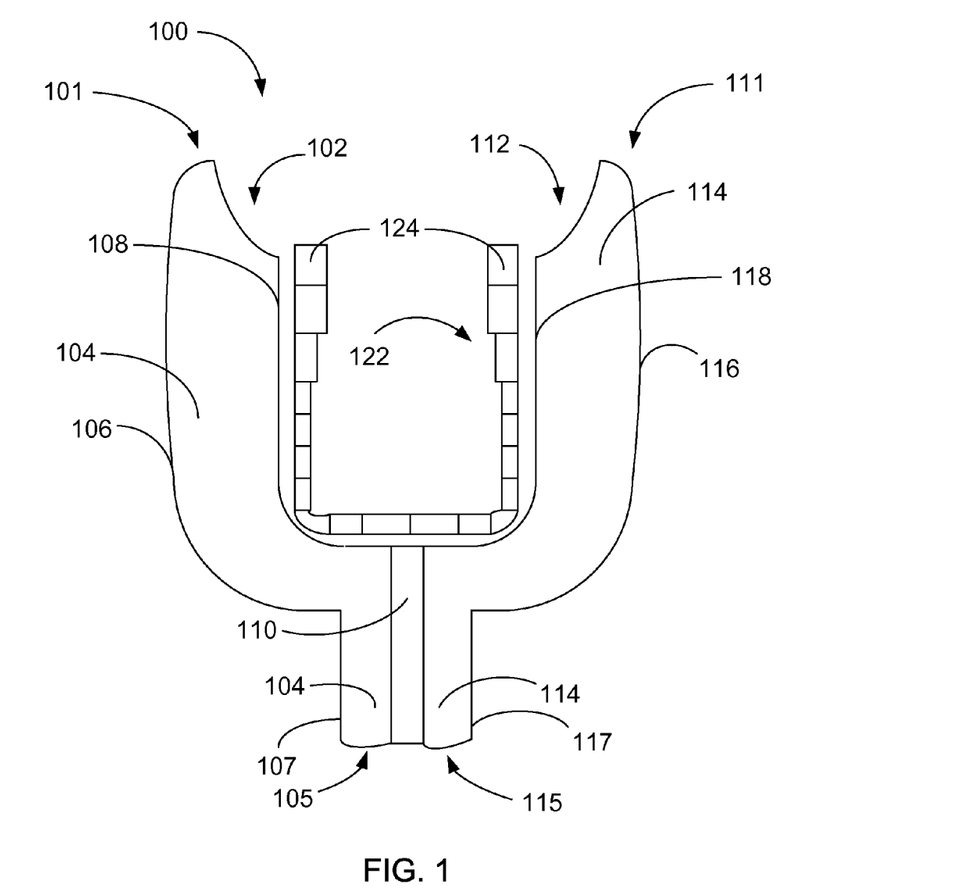
FIG. 1 illustrates a cross-sectional view of an embodiment of a breathing apparatus.

Right passageway 104 includes a right exit tube 107, a right inner passageway wall 108, and a right outer passageway wall 106. Right exit tube 107 is attached to right outer passageway wall 106, right inner passageway wall 108, and connector 110 as illustrated in FIG. 1. Right exit tube 107 is at one end of the right passageway 104 and forms the right exterior airway opening 105. During use, a portion of the right exit tube 107 extends from a patient's mouth. In one embodiment, the right exit tube 107 is also a handle for insertion and removal of the breathing apparatus 100 to and from a patient's mouth.

The right inner passageway wall 108 is shaped to contour around the left and/or right outside portion of the patient's teeth 122. The outside portion of the patient's teeth 122 is the portion of the teeth 122 that abuts the cheeks of the patient. The left outside portion of the patient's teeth 122 is the portion of teeth 122 located on the same side as the patient's left hand. The right outside portion of the patient's teeth 122 is the portion of teeth 122 located on the same side as the patient's right hand. In one embodiment, right inner passageway wall 108 is a flat wall that contours around the left and/or right outside portion of the patient's teeth 122. During use, right inner passageway wall 108 is adjacent to and/or abuts the left and/or right outside portion of the patient's teeth 122. The right inner passageway wall 108 is attached to the connector 110, the right exit tube 107, and the right outer passageway wall 106 as illustrated in FIG. 1.

The right outer passageway wall 106 is attached to right inner passageway wall 108 and right exit tube 107. The right outer passageway wall 106 and the right inner passageway wall 108 connect to form the right interior airway opening 102 on the end of the right airway tube 101 that is opposite right exit tube 107. The opposite end of the right outer passageway wall 106 connects to the right exit tube 107 and right inner passageway wall 108. A portion of right outer passageway wall 106 also contours around the left and/or right outside portion of patient's teeth 122. In one embodiment, when right outer passageway wall 106 reaches the back portion of the patient's teeth 124, right outer passageway wall 106 may curve to position the right interior airway opening 102 in the space between the patient's back teeth 524 and the back of the patient's mouth. In another embodiment, when right outer passageway wall 106 reaches the back portion of the patient's teeth 124, right outer passageway wall 106 may end to position the right interior airway opening 102 adjacent to the space formed between the patient's back teeth 524 and the back of the patient's mouth.

In one embodiment, the right outer passageway wall 106 is curved forming a semi-circle or semi-oval shaped wall. In the embodiment, with a right inner flat passageway wall 108, the right outer curved passageway wall 106 and the right inner flat passageway wall 108 attached to form a D-shaped passageway for a portion of right passageway 104 of right airway tube 101. In one aspect of this embodiment, the D-shaped passageway portion of right passageway 104 extends from right interior airway opening 102 to right exit tube 107.

The left airway tube 111 includes a left interior airway opening 112, a left exterior airway opening 115, and a left passageway 114. Left passageway 114 provides a flow path for air from the left interior airway opening 112 to the left exterior airway opening 115. This flow path allows air to travel to and from the inside of the patient's mouth to the exterior of the patient mouth during use.

The left exterior opening is positioned so that during use it is located outside of a patient's mouth. The left interior airway opening 112 is positioned so that during use the left interior airway opening 112 is located adjacent to, extends into, or extends through the left space behind the right-side and/or left-side of teeth 124 and the back of that side of the patient's mouth before becoming the throat. Behind the right-side and/or left-side of teeth 124, is a position behind the last upper and lower tooth on the right-side and/or left-side of the patient's mouth that is closest to a patient's throat.

Figure 2:
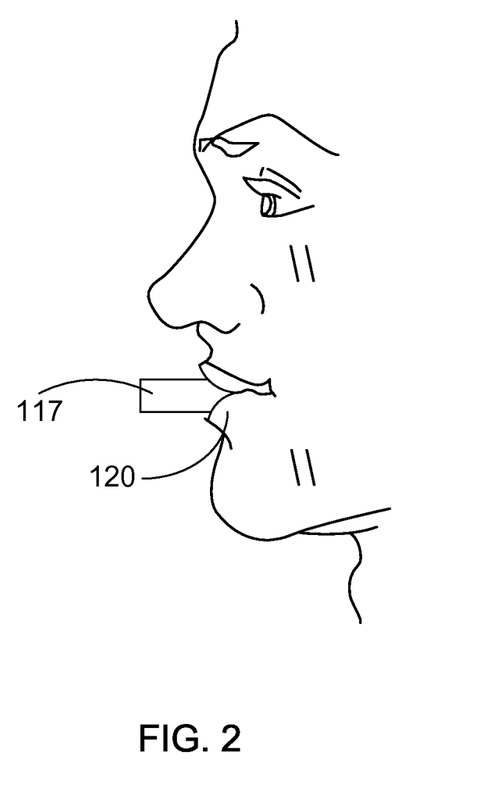
FIG. 2 illustrates a side view of an embodiment of a breathing apparatus during use.
Figure 3:
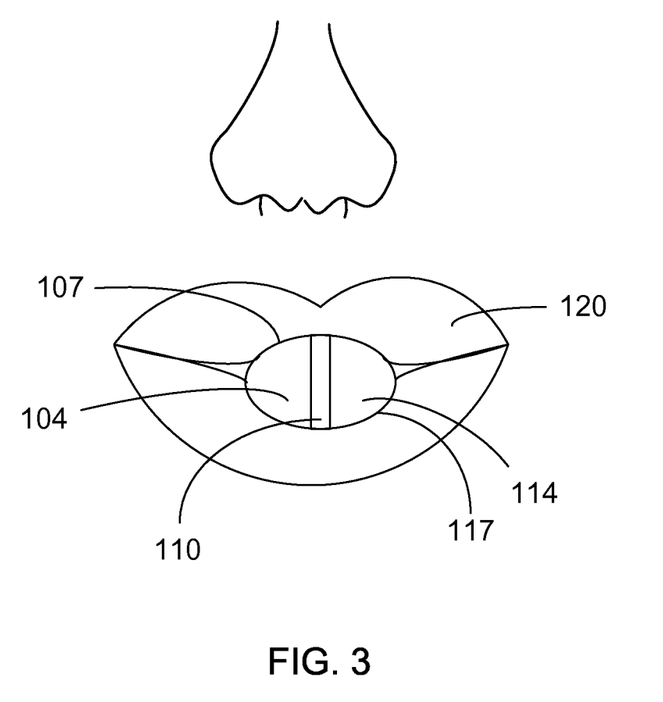
FIG. 3 illustrates a front view of an embodiment of a breathing apparatus during use.
Figure 4:
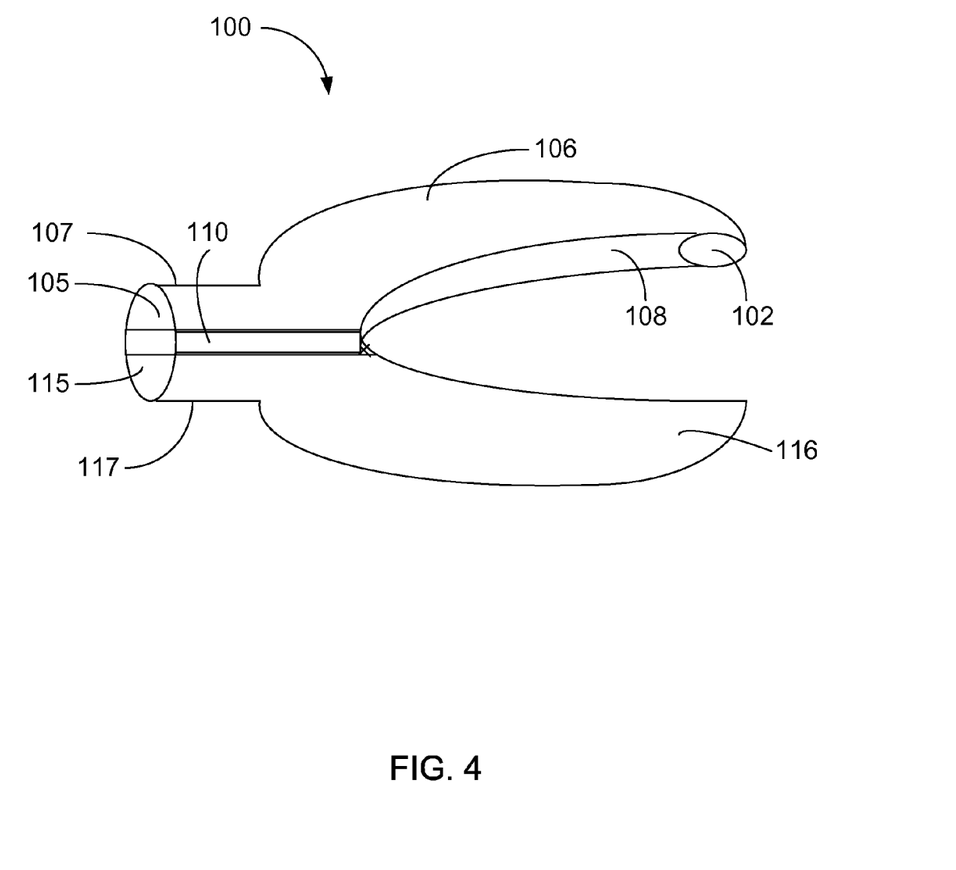
FIG. 4 illustrates a cross-sectional view of an embodiment of a breathing apparatus.

Left passageway 114 includes a left exit tube 117, a left inner passageway wall 118, and a left outer passageway wall 116. Left exit tube 117 is attached to left outer passageway wall 116, left inner passageway wall 118, and connector 110 as illustrated in FIG. 1. Left exit tube 117 is at one end of the left passageway 114 and forms the left exterior airway opening 115. During use, a portion of the left exit tube 117 extends out from a patient's lips 120 of the patient's mouth as illustrated in FIG. 2. In one embodiment, the left exit tube 117 is also a handle for insertion and removal of the breathing apparatus 100 to and from a patient's mouth.

The left inner passageway wall 118 is shaped to contour around the right and/or left outside portion of the patient's teeth 122. The outside portion of the patient's teeth 122 is the portion of the teeth 122 that abut the cheeks of the patient. In one embodiment, left inner passageway wall 118 is a flat wall that contour around the right and/or left outside portion of the patient's teeth 122. During use, left inner passageway wall 118 is adjacent to and/or abuts the right and/or left outside portion of the patient's teeth 122. The left inner passageway wall 118 is attached to the connector 110, the left exit tube 117, and the left outer passageway wall 116 as illustrated in FIG. 1.

The left outer passageway wall 116 is attached to left inner passageway wall 118 and left exit tube 117. The left outer passageway wall 116 and the left inner passageway wall 118 connect to form the left interior airway opening 112 on the end of the left airway tube 111 that is opposite left exit tube 117. The opposite end of the left outer passageway wall 116 connects to the left exit tube 117 and left inner passageway wall 118. A portion of right outer passageway wall 106 also contours around the right and/or left outside portion of patient's teeth 122. In one embodiment, when right outer passageway wall 106 reaches the back portion of the patient's teeth 124, right outer passageway wall 106 may curve to position the right interior airway opening 102 in the space between the patient's back teeth 524 and the back of the patient's mouth. In another embodiment, when right outer passageway wall 106 reaches the back portion of the patient's teeth 124, right outer passageway wall 106 may end to position the right interior airway opening 102 adjacent to the space between the patient's back teeth 524 and the back of the patient's mouth.

In one embodiment, the left outer passageway wall 116 is curved forming a semi-circle or semi-oval shaped wall. In the embodiment, with a left inner flat passageway wall 118, the left outer curved passageway wall 116 and the left inner flat passageway wall 118 attach to form a D-shaped passageway for a portion of left passageway 114 of left airway tube 111. In one aspect of this embodiment, the D-shaped passageway portion of left passageway 114 extends from left interior airway opening 112 to left exit tube 117.

The connector 110 attaches the right airway tube 101 to the left airway tube 111. Right airway tube 101 and left airway tube 111 are completely separate components with completely separate passageways and air flow paths, which are attached to each other via the connector 110. The connector 110 may be made of any suitable semi-rigid material for connecting the right airway tube 101 to the left airway tube 111, such as plastic and/or fabric. In one embodiment, the connector 110 is a connective plastic webbing. In another embodiment, the connector 110 is a woven fiber and plastic material.

In one embodiment, the connector 110 is designed to create easy separation between the right airway tube 101 and the left airway tube 111. In one embodiment, the connector 110 may be cut with scissors, a knife, and/or a razor separating right airway tube 101 from left airway tube 111. Once separated, right airway tube 101 and left airway tube 111 may be utilized individually or in combination depending upon the medical caregiver and/or patient's desires.

In an alternative embodiment, the breathing apparatus 100 includes only one airway tube, which may be utilized on either side of a patient's mouth and has no connective webbing. In this embodiment, one or two breathing apparatuses may be utilized in one patient at one time.

Figure 5:
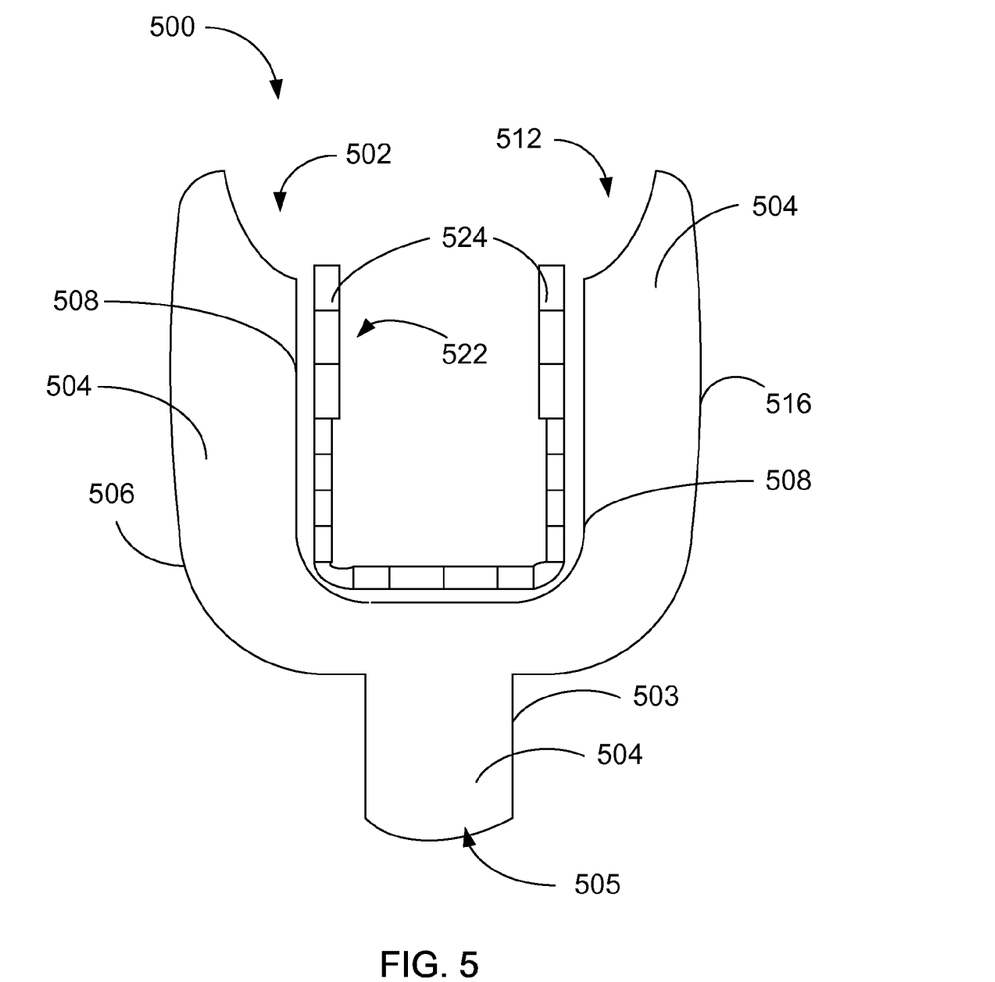
FIG. 5 illustrates a top, side view of an embodiment of a breathing apparatus.

FIG. 5 illustrates a top cross-sectional view an embodiment of a breathing apparatus 500. The breathing apparatus 500 is configured to provide for easy size adjustments based on patient mouth size. In one embodiment, the breathing apparatus 500 is made of a material that may be cut with scissors, a knife, and/or a razor. This embodiment, allows any end of the breathing apparatus 500 to be cut and/or shortened as needed. Accordingly, this embodiment, allows the breathing apparatus 500 to be easily adjusted for different mouth sizes prior to use for a more effective airflow and a more comfortable mouth fit for the patient.

In another embodiment, the right and left side of the breathing apparatus 500 are substantially mirror images of each other. As utilizes herein, the term "substantially mirror images" refers to a side of the breathing apparatus 500 that mirrors enough of the opposite side that either side of the breathing apparatus 500 can be utilized on either side of a patient's mouth.

Breathing apparatus 500 includes a right interior airway opening 512, a left interior airway opening 502, an exterior airway opening 505, and an air passageway 504. The air passageway 504 is formed by an exit tube 503, an inner flat passageway wall 508, a right curved passageway wall 516, and a left curved passageway wall 506. Further, the air passageway 504 connects right interior airway opening 512, left interior airway opening 502, and exterior airway opening 505. Accordingly, air passageway 504 provides a flow path for air to move to and from behind a patient's teeth 524 via the right and left interior airway openings 502, 512 and through the patient's mouth via the exterior airway opening 505 during use.

The exterior airway opening 505 is positioned so that during use it is located outside of a patient's mouth. The right and left interior airway openings 102, 112 are positioned so that during use the right and/or left interior airway openings 102, 112 are located adjacent to, extends into, or extends through the left and right space behind the right-side and left-side of teeth 524 and the back side of the patient's mouth before becoming the throat.

Exit tube 503 is attached to the left curved passageway wall 506 and right curved passageway wall 516 as illustrated in FIG. 5. In one embodiment, the exit tube 503 can further connect to the inner flat passageway wall 508. Exit tube 503 is at the front end of the breathing apparatus 500 and forms the exterior airway opening 505. During use, a portion of the exit tube 503 extends from a patient's mouth. In one embodiment, the exit tube 503 can also act as a handle for insertion and removal of the breathing apparatus 500 into and from a patient's mouth.

Inner flat passageway wall 508 is shaped to contour around the outside portion of the patient's teeth 522. Further, inner flat passageway wall 508 is a flat wall that contours around the outside portion of the patient's teeth 522. During use, inner flat passageway wall 508 is adjacent to and/or abuts the outside portion of the patient's teeth 522. The inner flat passageway wall 508 is attached to left curved passageway wall 506 and right curved passageway wall 516 as illustrated in FIG. 5.

The left curved passageway wall 506 is attached to inner flat passageway wall 508 and exit tube 503. The left curved passageway wall 506 and the inner flat passageway wall 508 connect to form a portion of air passageway 504 and interior airway opening 502 on one end of the breathing apparatus 500 that is opposite exit tube 503. The opposite end of the left exterior passageway wall 506 connects to exit tube 503 and the inner flat passageway wall 508. At least a portion of left curved passageway wall 506 also contours around the left and/or left outside portion of patient's teeth 522. In one embodiment, when left curved passageway wall 506 reaches the back portion of the patient's teeth 524, the left curved passageway wall 506 curves to position the left interior airway opening 502 in the space between the back of the patient's teeth 524 and the back of the patient's mouth. In another embodiment, when left curved passageway wall 506 reaches the back portion of the patient's teeth 524, the left curved passageway wall 506 ends to position the left interior airway opening 502 adjacent to the space formed between the back of the patient's teeth 524 and the back of the patient's mouth.

Left curved passageway wall 506 is curved to form a semi-circle or semi-oval shaped wall. Accordingly, left outer curved passageway wall 506 and inner flat passageway wall 508 attach to form a D-shaped tube for a portion of air passageway 504 of breathing apparatus 500. The D-shaped portion of air passageway 504 extends from left interior airway opening 502 to exit tube 503.

The right curved passageway wall 516 is attached to inner flat passageway wall 508 and exit tube 503. The right curved passageway wall 516 and the inner flat passageway wall 508 connect to form a portion of air passageway 504 and right interior airway opening 512 on one end of the breathing apparatus 500 that is opposite exit tube 503. The opposite end of the right curved passageway wall 516 connects to exit tube 503 and inner flat passageway wall 508. At least a portion of right curved passageway wall 516 also contours around the left and/or right outside portion of patient's teeth 522. In one embodiment, when right curved passageway wall 516 reaches the back portion of the patient's teeth 524, right curved passageway wall 516 curves to position the right interior airway opening 512 in the space between the back of the patient's teeth 524 and the back of the patient's mouth. In another embodiment, when right curved passageway wall 516 reaches the back portion of the patient's teeth 524, the right curved passageway wall 516 ends to position the right interior airway opening 512 adjacent to the space formed between the back of the patient's teeth 524 and the back of the patient's mouth.

Right curved passageway wall 516 is curved to form a semi-circle or semi-oval shaped wall. Accordingly, right curved passageway wall 516 and inner flat passageway wall 508 attach to form a D-shaped tube for a portion of air passageway 504 of breathing apparatus 500. The D-shaped portion of air passageway 504 extends from left interior airway opening 502 to exit tube 503.

EXAMPLE EMBODIMENT

Figure 6:
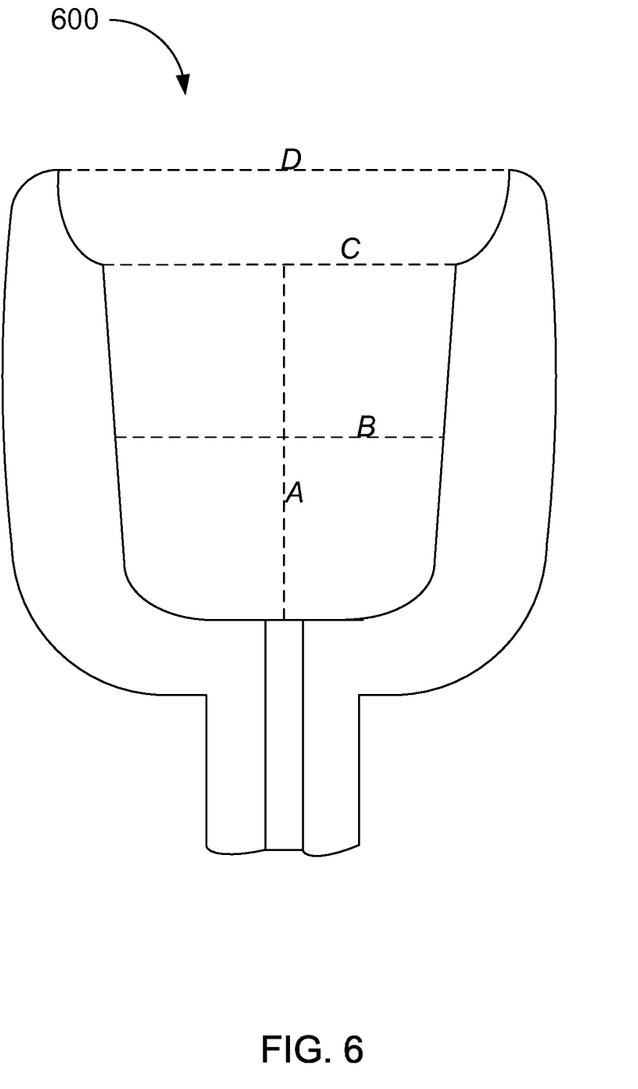
FIG. 6 illustrates a top, side view of an embodiment of a breathing apparatus.

FIG. 6 illustrates an example embodiment of a breathing apparatus 600.

This example embodiment, demonstrates example sizing that may be utilized to form breathing apparatus 600. The measurements disclosed below are merely exemplary and are in no way meant to be limiting to the disclosure. The sizes provided are example dimensions for an adult breathing apparatus 600. In this embodiment, the right and left interior airway openings have a diameter of about 0.75 inches. The right and left passageways have a width of about 5/16 inches. The right and left passageways have a height of about 7/16 inches. The connector has a width of about 1/8 inches. In this exemplary embodiment, the right and left exterior airway openings have a diameter and/or width of 0.44 inches. Further, all of the walls in breathing apparatus 600 have a thickness of about 1/16 inches.

The distance between the right and left inner passageway wall may vary depending upon the point from which you measure. In this embodiment, at line B, around the center of the right and left inner passageway walls, the distance between the two walls is about 1¾ inches. In this embodiment, at line C, at the end of the right and left inner passageway walls at right and left interior airway openings, the distance between the right and left inner passageway walls is about 2¼ inches. The distance between right and left outer passageway walls at right and left interior airway openings or line D is about 2¾ inches. Line A, as illustrated in FIG. 6, represents the distance from the connector to line C. Line A, in this embodiment, is about 1⅝ inches.

Again, the sizes listed are merely exemplary. These sizes may vary for different applications, such as breathing apparatus designed for children, young adults, females, males, and infants.

Those skilled in the art will recognize that the apparatus of the present disclosure may be implemented in many manners and as such are not to be limited by the foregoing exemplary embodiments and examples. Any number of the features of the different embodiments described herein may be combined into single or multiple embodiments, and alternate embodiments having fewer than or more than all of the features herein described are possible.

While various embodiments have been described, various changes and modifications may be made which are well within the scope of the present disclosure. Numerous other changes may be made which will readily suggest themselves to those skilled in the art and which are encompassed in the spirit of the disclosure and as defined in the appended claims.

What is claimed is:

1. A breathing assistance apparatus, comprising:
    a right airway tubing including:
        a right interior airway opening,
        a right exterior airway opening, and
        a right passageway connecting the right interior airway opening and the right exterior airway opening, the right passageway including:
            a right exit tube,
            a right inner flat passageway wall connected to the right exit tube adapted to contour around a right outside portion of the patient's teeth, and
            a right outer curved passageway wall adapted to contour around the right outside portion of the patient's teeth and connected to the right flat passageway wall and the right exit tube,
            wherein the right passageway provides a flow path for air adapted to move the air to and from behind a right side of a patient's teeth via the right interior airway opening via the right exterior airway opening during use;
    a left airway tubing including:
        a left interior airway opening,
        a left exterior airway opening, and
        a left passageway connecting the left interior airway opening and the left exterior airway opening, the left passageway including:
            a left exit tube,
            a left inner flat passageway wall connected to the left exit tube adapted to contour around a left outside portion of the patient's teeth, and
            a left curved passageway wall connected to the left flat passageway wall and the left exit tube adapted to contour around the left outside portion of the patient's teeth;
            wherein the left passageway provides a flow path for air adapted to move the air to and from behind a left side of a patient's teeth via the left interior airway opening via the left exterior airway opening during use,
    wherein the right airway tubing and the left airway tubing are made of a semi-rigid material that is adapted to provide the flow path located between the patient's teeth and cheeks; and
    a connector, the connector attaching the right airway tubing to the left airway tubing; said connector spanning from the right exterior airway opening and the left exterior airway opening to a juncture of the right inner flat passageway wall and the left inner flat passageway wall.

2. The breathing assistance apparatus of claim 1, wherein the connector is connective webbing.

3. The breathing assistance apparatus of claim 1, wherein the connector allows the left airway tubing to be separated from the right airway tubing.

4. The breathing assistance apparatus of claim 1, wherein the right airway tubing and the left airway tubing are the mirror images of each other.

5. The breathing assistance apparatus of claim 1, wherein the right airway tubing and the left airway tubing are made of a semi-rigid plastic material that is configured to be cut with scissors.

6. The breathing assistance apparatus of claim 1, wherein the right exterior airway opening and the left exterior airway opening are adapted to be located outside of a patient's mouth during use.

7. The breathing assistance apparatus of claim 1, wherein the right interior airway opening and the left interior airway opening are adapted to extend at least partially through a space behind the teeth of the patient during use.

8. The breathing assistance apparatus of claim 1, wherein the right interior airway opening and the left interior airway opening are adapted to be positioned adjacent to a space behind the teeth of the patient during use.

9. A breathing assistance apparatus, comprising:
    a left airway tubing, the left airway tubing including:
        a left interior airway opening,
        a left exterior airway opening, and
        a left passageway connecting the left interior airway opening and the left exterior airway opening, the left passageway including:
            a left exit tube,
            a left curved outer passageway wall connected to the left exit tube adapted to contour around a left outside portion of the patient's teeth, and
            a left inner flat passageway wall connected to the left outer passageway wall and the left exit tube,
            wherein the left passageway provides a flow path for air adapted to move the air to and from behind a left side of a patient's teeth via the left interior airway opening via the left exterior airway opening during use;
    a right airway tubing including:
        a right interior airway opening,
        a right exterior airway opening, and
        a right passageway connecting the right interior airway opening and the right exterior airway opening, the right passageway including:
            a right exit tube,
            a right inner flat passageway wall connected to the right exit tube adapted to contour around a right outside portion of the patient's teeth, and
            a right outer curved passageway wall adapted to contour around the right outside portion of the patient's teeth and connected to the right flat passageway wall and the right exit tube,
            wherein the right passageway provides a flow path for air adapted to move the air to and from behind a right side of a patient's teeth via the right interior airway opening via the right exterior airway opening during use; and
    a connector, the connector attaching the right airway tubing to the left airway tubing;

said connector spanning from the right exterior airway opening and the left exterior airway opening to a juncture of the right inner flat passageway wall and the left inner flat passageway wall.

10. The breathing assistance apparatus of claim 9, wherein the left interior airway opening is curved.

11. The breathing assistance apparatus of claim 9, wherein an elbow is formed by the connection of the left exit tube to the left outer passageway wall and the left inner passageway wall.

12. The breathing assistance apparatus of claim 9, wherein the left exit tube is a handle for insertion and removal of the breathing apparatus.

13. The breathing assistance apparatus of claim 9, wherein the right airway tubing and the left airway tubing are made of a semi-rigid plastic material that is configured to be cut with scissors.

14. The breathing assistance apparatus of claim 9, wherein the right the right exterior airway opening and the left exterior airway opening are adapted to be located outside of the patient's mouth during use.

15. The breathing assistance apparatus of claim 9, wherein the right interior airway opening and the left interior airway opening are adapted to extend at least partially through a space behind the teeth of the patient during use.

16. The breathing assistance apparatus of claim 9, wherein the right interior airway opening and the left interior airway opening are adapted to be adjacent to a space behind the teeth of the patient during use.

\* \* \* \* \*